United States Patent [19]

Bartsch et al.

[11] Patent Number: 5,547,846
[45] Date of Patent: Aug. 20, 1996

[54] IMMUNOGENIC REGIONS ON THE E7 PROTEIN OF HUMAN PAPILLOMAVIRUS TYPE 16

[75] Inventors: Dusan Bartsch, Heidelberg; Lutz Gissmann, Wiesloch; Martin Müller, Heidelberg, all of Germany

[73] Assignee: Behringwerke Aktiengesellschaft, Marburg, Germany

[21] Appl. No.: 292,169

[22] Filed: Aug. 16, 1994

Related U.S. Application Data

[63] Continuation of Ser. No. 144,503, Nov. 2, 1993, abandoned, which is a continuation of Ser. No. 490,444, Mar. 8, 1990, abandoned.

[30] Foreign Application Priority Data

Mar. 10, 1989 [DE] Germany ............... 39 07 721.7

[51] Int. Cl.$^6$ ............... C12Q 1/00; G01N 33/53; C07K 16/08; C07K 7/02
[52] U.S. Cl. ............... 435/7.1; 530/387.1; 530/387.9; 530/326; 530/327; 530/328; 436/547; 436/512
[58] Field of Search ............... 530/387.1, 387.9, 530/326, 327, 328; 436/547, 512; 435/7.1

[56] References Cited

FOREIGN PATENT DOCUMENTS

0257754A2  3/1988  European Pat. Off. .
0402132A2  12/1990  European Pat. Off. .

OTHER PUBLICATIONS

K. Seedorf et al., EMBO J. 6(1):139–144 (1987).
V. Krchnak et al., J. Gen. Virol. 71:2719–24 (1990).
M. Muller et al., J. Gen. Virol. 71:2709–17 (1990).
M. Durst et al., Proc. Natl. Acad. Sci. USA 80:3812–3815 (1983).
K. Seedorf et al., Virol. 145:181–185 (1985).
D, Smotkin and F. O. Wettstein Proc. Natl. Acad. Sci. USA 83:4680–4684 (1986).
K. Seedorf et al., EMBO J. 6:139–144 (1987).
G. P. Smith, Science 228:1315–1317 (1985).
Lerner, Nature vol. 299 1982 p. 592.
Oltersdorf et al. (I) J. General Virology 68(11) 2933–8 1987.
Oltersdorf et al. (II) Ger. Offen. 5 pp. 1989, Jan. 1.
Voller et al. Enzyme Immunoassays in diagnostic Medicine vol. 53 1976, p. 3418.

Primary Examiner—Lila Feisee
Attorney, Agent, or Firm—Finnegan, Henderson, Farabow, Garrett & Dunner, L.L.P.

[57] ABSTRACT

The invention describes two immunogenic regions of the E7 protein of human papillomavirus type 16 (HPV 16), one immunoreactive region being located downstream from nucleotide 595 and the other being located downstream from nucleotide 667 of the HPV 16 genome.

4 Claims, No Drawings

IMMUNOGENIC REGIONS ON THE E7 PROTEIN OF HUMAN PAPILLOMAVIRUS TYPE 16

This application is a continuation of application Ser. No. 08/144,503 filed Nov. 2, 1993, now abandoned, which is a continuation of application Ser. No. 07/490,444 filed Mar. 8, 1990, abandoned.

The invention relates to two immunogenic regions on the human papillomavirus type 16 (HPV 16) E7 protein, with one immunoreactive region being located 3' of nucleotide position 595 and the other being located 3' of nucleotide position 667 of the HPV 16 genome.

Papillomaviruses cannot be grown in culture. Hence genetic engineering methods are a prerequisite for the use of HPV DNA as a diagnostic aid and for obtaining the expression products, the use thereof as antigens, the isolation of antibodies and the preparation of corresponding diagnostic aids.

Dürst et al., Proc. Natl. Acad. Sci. USA 80 (1983) 3813–3815 describe a new type of human papillomavirus (HPV) which they call HPV 16. The DNA sequence and the genome organization of this virus are reproduced in Seedorf et al., Virology 145 (1985) 181–185.

Smotkin and Wettstein, Proc. Natl. Acad. Sci. USA 83, 4680–4684 (1986) identified the E7 transcript as the most frequently occurring HPV transcript in the CaSki cell line and another cervical carcinoma which contains the HPV 16 DNA mainly as plasmid. Seedorf et al., EMBO J. 6, 139–144 (1987) then showed that the E7 protein is the most frequently occurring vital HPV 16 protein in those cell lines which contain HPV 16 in integrated form or as plasmid.

The E7 protein appears additionally to play a part in the maintenance of the transformed phenotype. In addition, antibodies against E7 protein are common in patients with cervical carcinoma. The detection of HPV 16 E7 protein or the antibodies directed against it is therefore of interest in diagnosis.

On analysis of a shotgun expression bank of cloned HPV 16 DNA with a polyclonal antiserum against HPV16 E7 of rabbits, two immunoreactive regions were found within the E7 protein. The first region is in the N-terminal section of E7 and is represented by four phage clones of different sizes:

I. 5'-ATG TTA GAT TTG CAA CCA GAG ACA ACT GAT CTC TAC TGT TAT GAG CAA-3'
II. 5'-ATG TTA GAT TTG CAA CCA GAG ACA ACT GAT CTC TAC
III. 5'-ATG TTA GAT TTG CAA CCA GAG ACA ACT
IV. 5'-ATG TTA GAT TTG CAA CCA GAG ACA

In these the 5' end of the clones corresponds to nucleotide position 595 on the HPV 16 genome.

Correspondingly, the amino acid sequence of the four classes is:

I. met leu asp leu gln pro glu thr thr asp leu tyr cys tyr glu gln
II. met leu asp leu gln pro glu thr thr asp leu tyr
III. met leu asp leu gln pro glu thr thr
IV. met leu asp leu gln pro glu thr The second immunoreactive region of HPV 16 E7 was located at nucleotide position 667 on the HPV 16 genome:

5'-GAT GAA ATA GAT GGT CCA GCT GGA CAA GCA GAA CCG GAC AGA GCC CAT TAC-3' and contains the 17 amino acids:

asp glu ile asp gly pro ala gly gln ala glu pro asp arg ala his tyr

The invention accordingly relates to the abovementioned two immunoreactive regions, and the use thereof for diagnosis, therapy and as pharmaceuticals or vaccines.

The invention is furthermore contained in the examples and patent claims.

EXAMPLES

1. Preparation of the shotgun expression bank of the HPV 16 genome.

The HPV 16 DNA cloned in the bacterial plasmid vector sp65 was converted into an average fragment size of about 100 base-pairs (bp) by ultrasonic shearing and subsequent DNase I treatment.

The ends of these fragments were filled in using T4 DNA polymerase and E. coli DNA ligase. The phage expression vector fd-tet-J6 was cut with Pvu II, and blunt ligationing of the fragments was carried out. fd-tet-J6 is derived from the bacteriophage fd and has been described by G. P. Smith, Science 228, 1315–1317 (1985).

2. Detection of immunogenic reactions

After the recombinant phages had been plated out on E. coli K91, replicas on nitrocellulose filters were investigated for immunoreactive phages using specific sera. 200 recombinants reacted with the antiserum; 30 of these were further investigated by DNA sequence analysis.

The following results were obtained:

1. All recombinants contain E7-specific sequences.

2. Two immunogenic regions were found within the E7 protein. The first region was identified by means of 25 overlapping clones. These 25 clones could be divided into 4 classes:

I. 5'-ATG TTA GAT TTG CAA CCA GAG ACA ACT GAT CTC TAC TGT TAT GAG CAA-3'
II. 5'-ATG TTA GAT TTG CAA CCA GAG ACA ACT GAT CTC TAC
III. 5'-ATG TTA GAT TTG CAA CCA GAG ACA ACT
IV. 5'-ATG TTA GAT TTG CAA CCA GAG ACA

In these the 5' end of the clones corresponds to nucleotide position 595 on the HPV 16 genome.

Correspondingly, the amino acid sequence of the four classes is:

I. met leu asp leu gln pro glu thr thr asp leu tyr cys tyr glu gln
II. met leu asp leu gln pro glu thr thr asp leu tyr
III. met leu asp leu gln pro glu thr thr
IV. met leu asp leu gln pro glu thr The minimum size of this region is therefore 8 amino acids. Since monoclonal antibodies reacted only with class I and II, but the polyclonal antiserum reacted with all 4 classes, there are at least 2 different epitopes located on the antigen of class I or II.

A synthetic oligopeptide (met-leu-asp-leu-gln-pro-glu-thr-thr-asp-leu-tyr) corresponding to the amino acid sequence of class II was used in an ELISA and showed a distinct reaction with the abovementioned polyclonal rabbit serum against HPV 16 E7.

The second immunoreactive region of 17 amino acids was found in 5 clones and was located at nucleotide position 667 on the HPV 16 genome:

5'-GAT GAA ATA GAT GGT CCA GCT GGA CAA GCA GAA CCG GAC AGA GCC CAT TAC-3' corresponding to the 17 amino acids asp glu ile asp gly pro ala gly gln ala glu pro asp arg ala his tyr

We claim:

1. An immunogenic sequence of HPV 16 E7 protein consisting of one of the following amino acid sequences:

I. met leu asp leu gln pro glu thr thr asp leu tyr cys tyr glu gln;

II. met leu asp leu gln pro glu thr thr asp leu tyr;

III. met leu asp leu gln pro glu thr thr; or

IV. met leu asp leu gln pro glu thr.

2. A diagnostic aid for detecting specific antibodies against HPV 16 E7 proteins, comprising a peptide consisting of an amino acid sequence as claimed in claim 1.

3. A monoclonal antibody which binds to an immunogenic sequence as claimed in claim 1.

4. A diagnostic aid comprising a monoclonal antibody as claimed in claim 3.

* * * * *